(12) United States Patent
Brice et al.

(10) Patent No.: US 7,897,357 B2
(45) Date of Patent: Mar. 1, 2011

(54) ASSAY FOR DETECTING IMMUNE RESPONSES INVOLVING ANTIGEN SPECIFIC CYTOKINE AND/OR ANTIGEN SPECIFIC CYTOKINE SECRETING T-CELLS

(75) Inventors: Gary Todd Brice, Alexandria, VA (US); Denise L. Doolan, Rockville, MD (US); Stephen L. Hoffman, Gaithersburg, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 285 days.

(21) Appl. No.: 09/978,669

(22) Filed: Oct. 18, 2001

(65) Prior Publication Data
US 2003/0143641 A1 Jul. 31, 2003

Related U.S. Application Data

(60) Provisional application No. 60/241,001, filed on Oct. 18, 2000.

(51) Int. Cl.
*G01N 33/53* (2006.01)
(52) U.S. Cl. .......................................... 435/7.2
(58) Field of Classification Search .................. None
See application file for complete search history.

(56) References Cited

OTHER PUBLICATIONS

Amichay et al. (1996) J. Immunology 157:4511-4520.*
Lauw, et al., The CXC Chemokines Gamma Interferon (IFN-Y) - Inducible Protein 10 and Monokine Induced by IFN-Y Are Released during Severe Melioidosis, *Infection and Immunity*, vol. 68, No. 7, Jul. 2000, pp. 3888-3893.

* cited by examiner

*Primary Examiner* — Michael Pak
(74) *Attorney, Agent, or Firm* — Joseph K. Hemby; Ning Yang; Albert Churilla

(57) ABSTRACT

Here, we describe a sensitive and specific assay and kit for the detection of chemokines having activity that is upregulated by Th-1 cytokines (such IFN-γ) and chemokines that upregulate the activity of Th-1 cytokines (such as IFN-γ). In a typical embodiment, detection of the chemokine monokine induced by gamma interferon (MIG) provides a measure of the biological effect of IFN-γ rather than direct quantitation of IFN-γ or IFN-γ secreting cells per se. Upregulation of MIG expression was observed following in vitro activation of PBMC with defined $CD8^+$ T cell epitopes derived from influenza virus, CMV, or EBV, and in all cases this was antigen-specific, genetically restricted and dependent on both $CD8^+$ T cells and IFN-γ. Responses as assessed by the MIG assay paralleled those detected by conventional IFN-γ ELISPOT, but the magnitude of response and sensitivity of the MIG assay were superior. Our data validate this novel method for the detection of high as well as low levels of antigen-specific and genetically restricted IFN-γ activity or MIG.

35 Claims, 10 Drawing Sheets

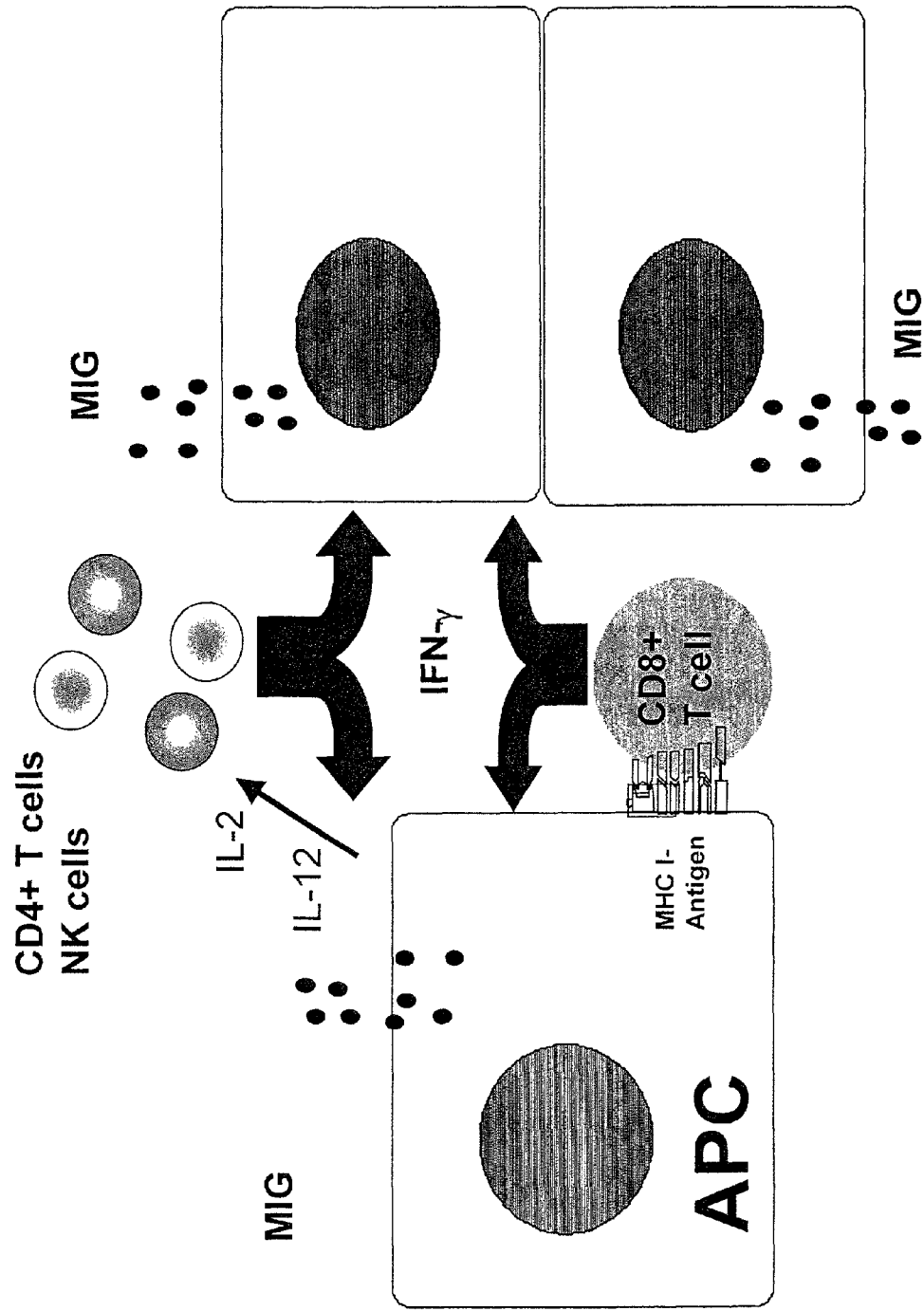
Figure 1. Diagram depicting antigen-specific induction of MIG expression mediated through biological amplification of IFN-γ responses.

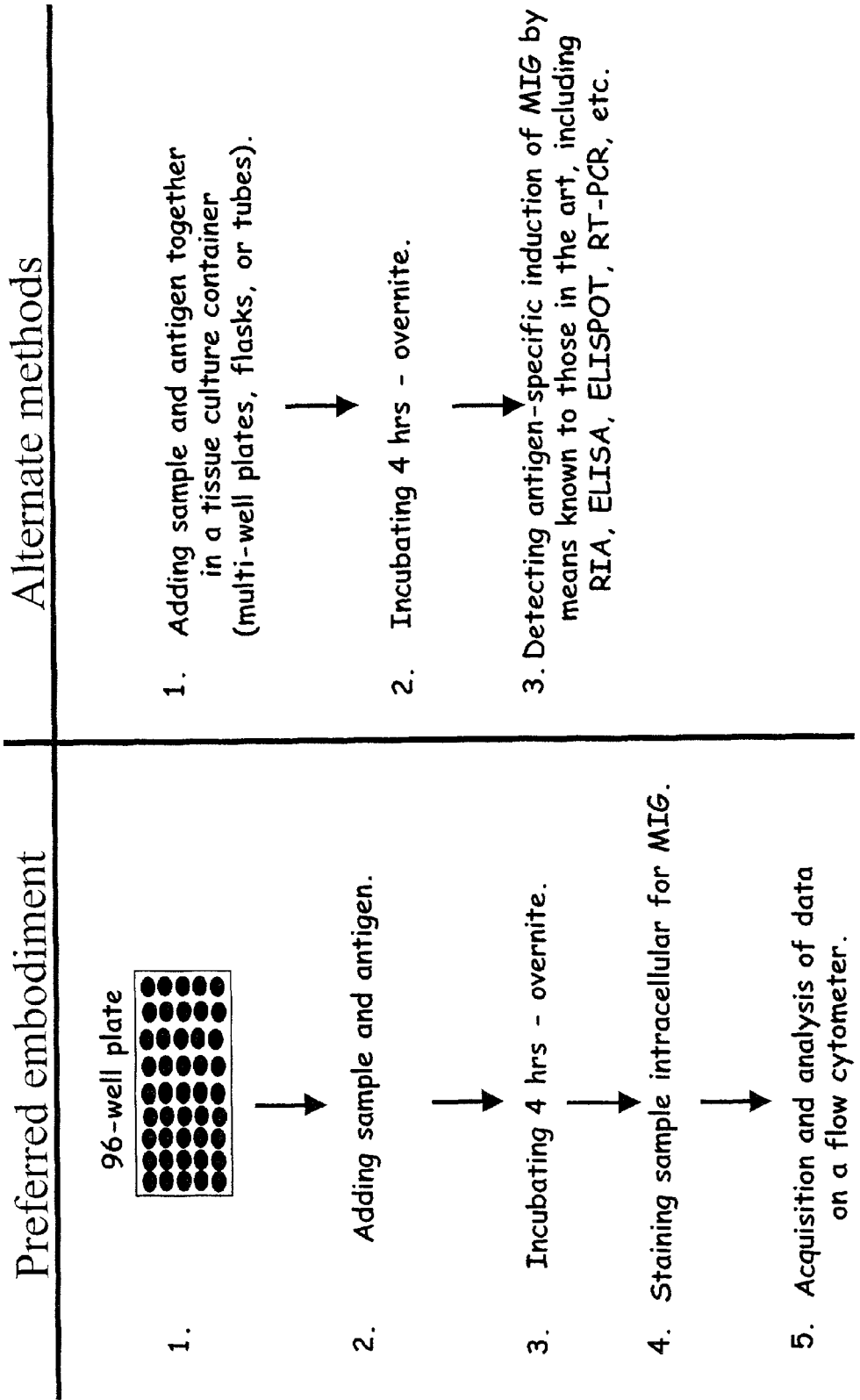
Figure 2. Schematic of the MIG assay

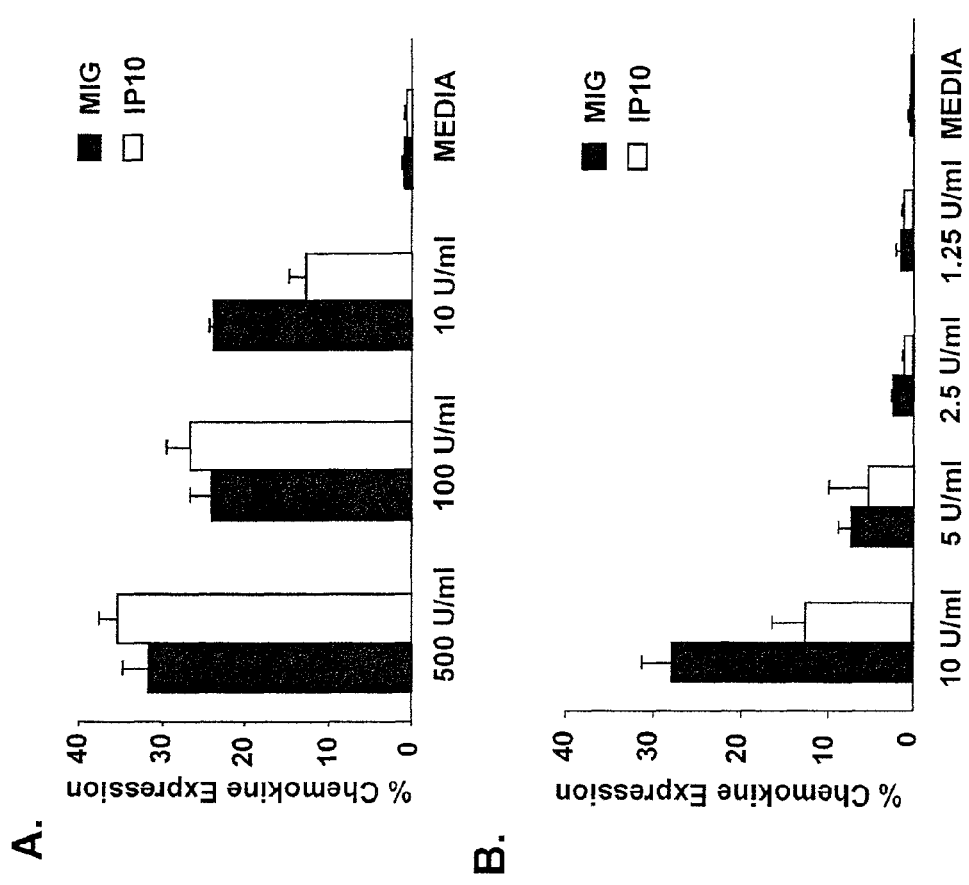
Figure 3. Induction of Chemokine Expression by IFN-γ

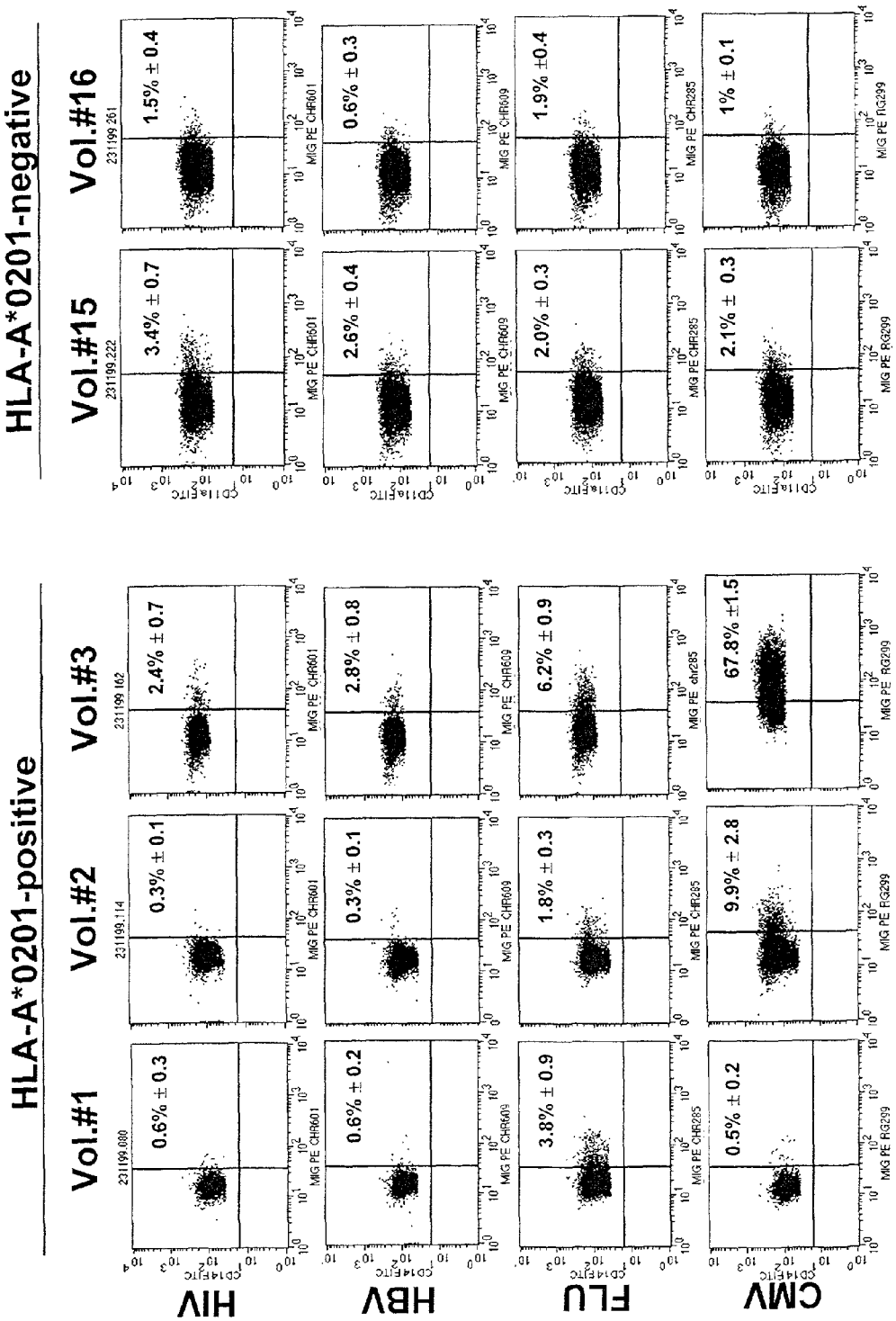
Figure 4. Antigen-specific, genetically-restricted induction of MIG expression.

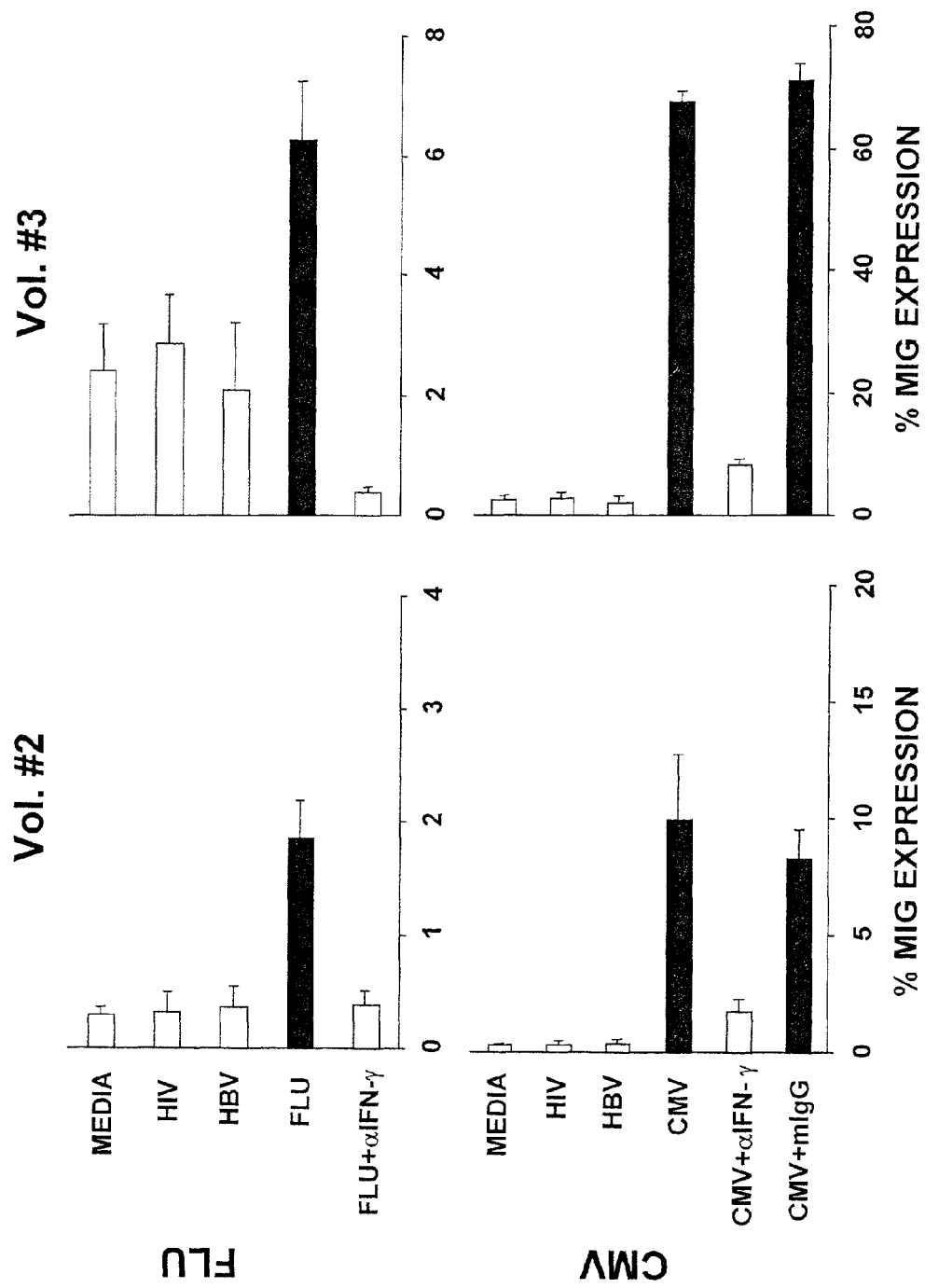
Figure 5. Requirement of IFN-γ for antigen-specific induction of MIG expression.

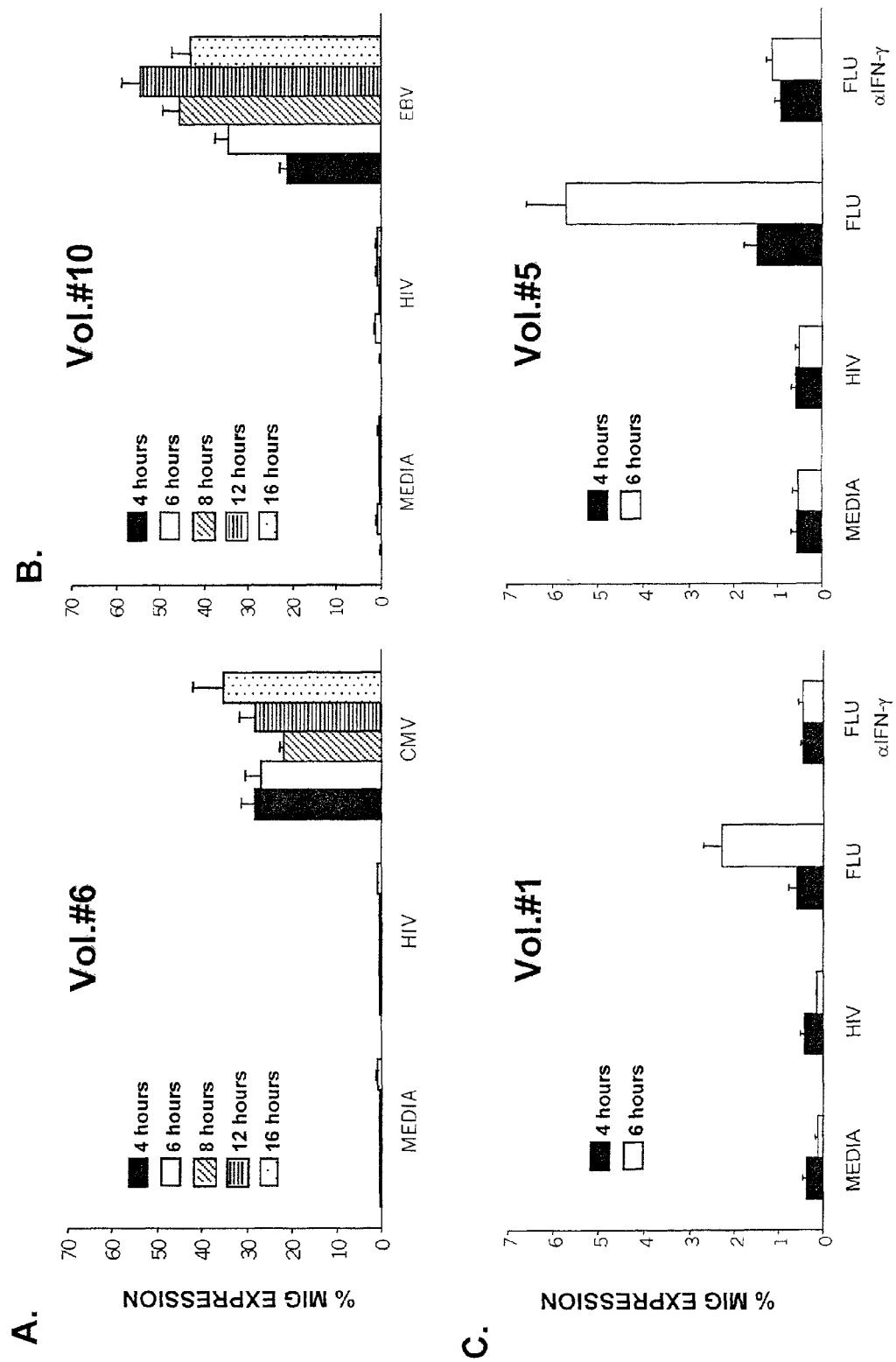
Figure 6. Kinetics of antigen-specific induction of MIG.

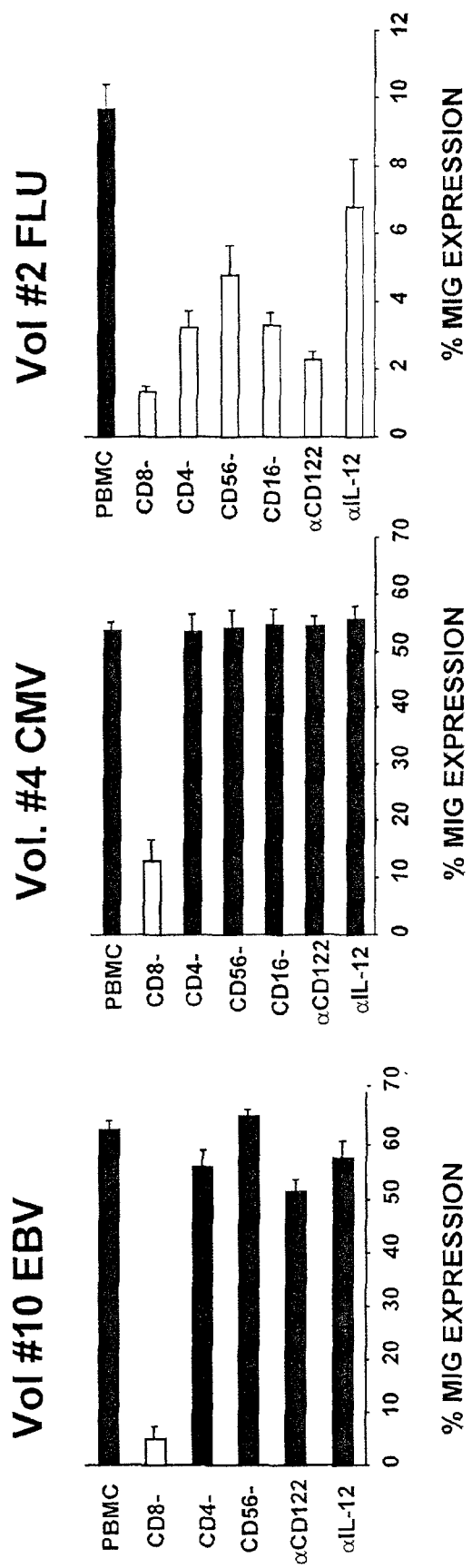
Figure 7. Cellular mechanism of antigen-specific induction of MIG expression.

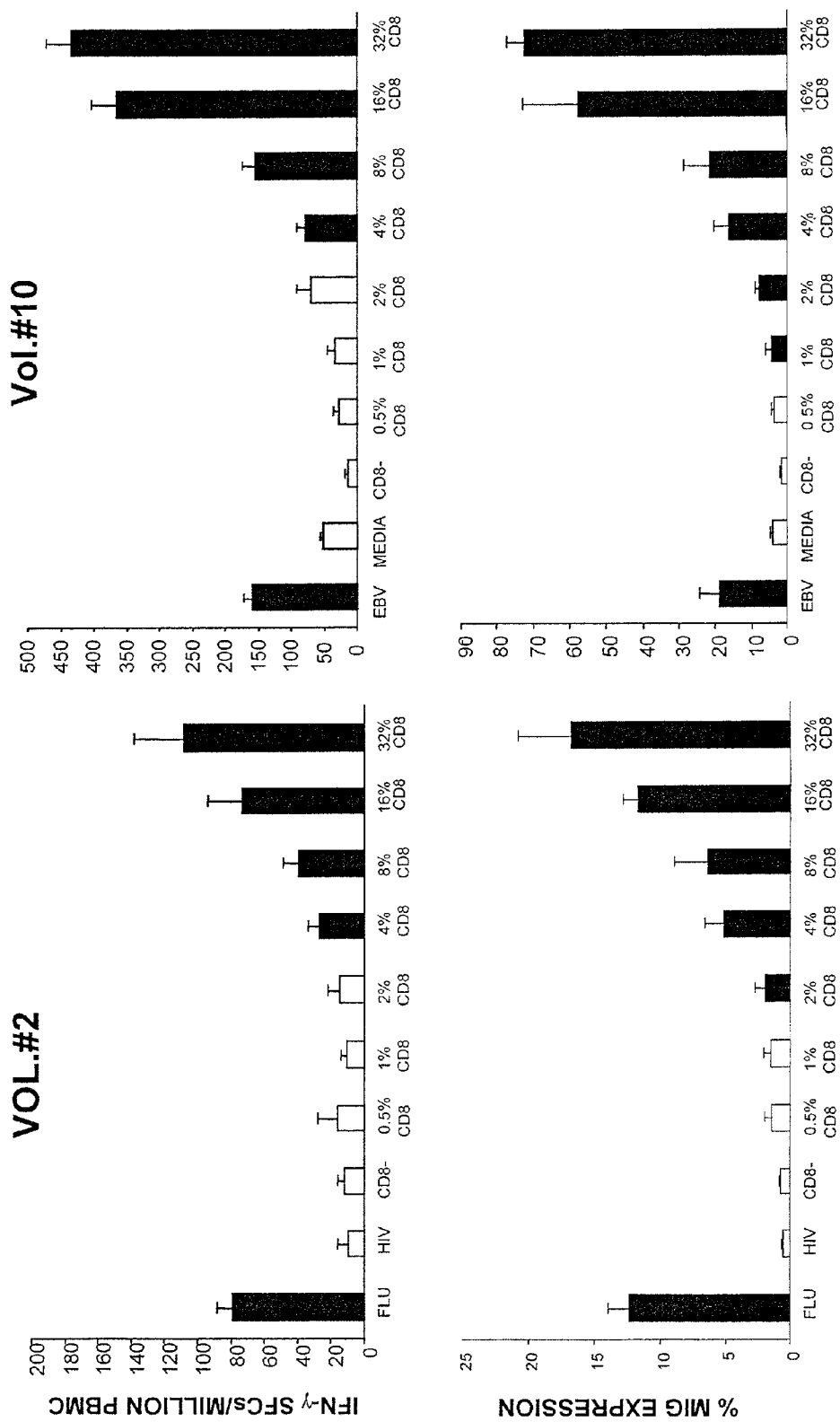
Figure 8. Effect of selective CD8+ T cell depletion/reconstitution experiments on the antigen-specific induction of MIG expression

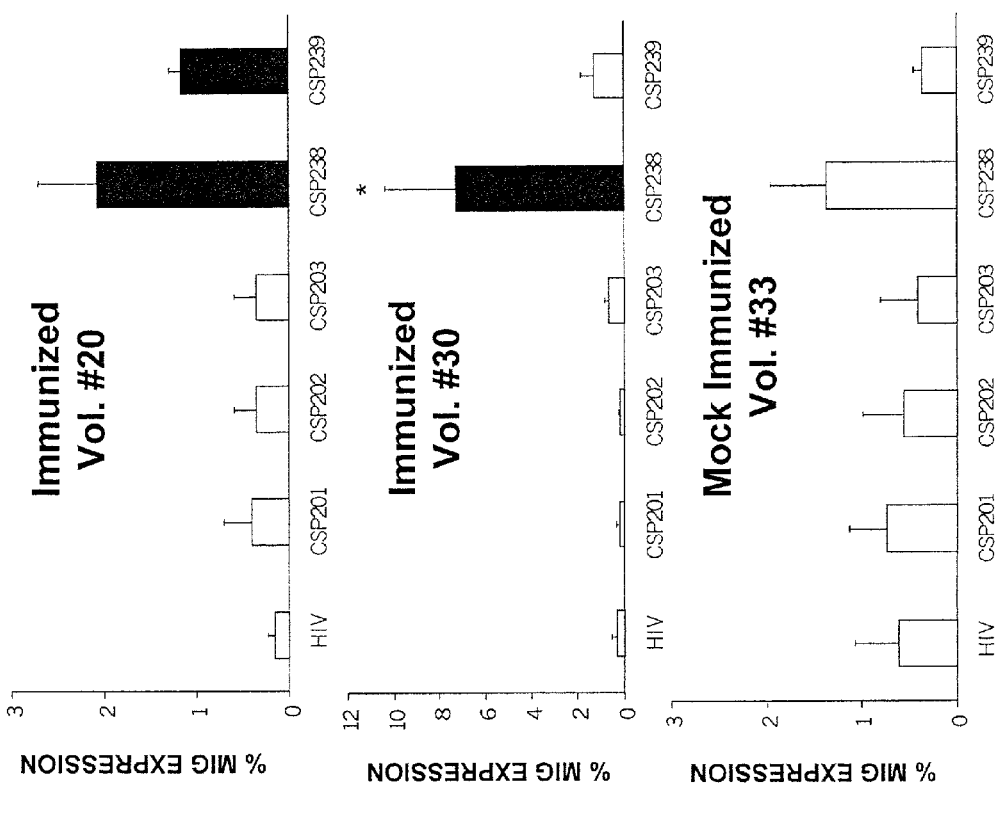
Figure 9. Antigen-specific induction of MIG expression in a experimental vaccine model against malaria.

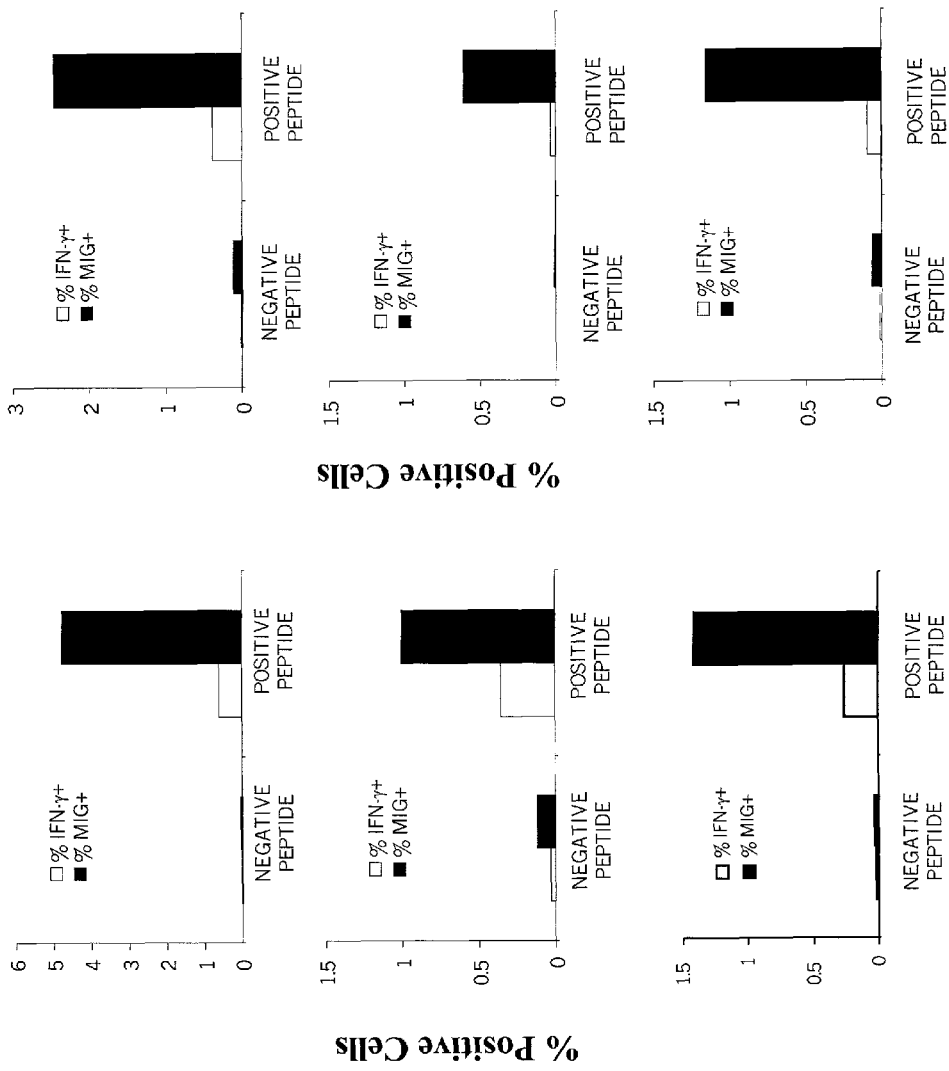
Figure 10. Induction of antigen-specific induction of MIG expression using whole blood stimulation protocols.

ASSAY FOR DETECTING IMMUNE RESPONSES INVOLVING ANTIGEN SPECIFIC CYTOKINE AND/OR ANTIGEN SPECIFIC CYTOKINE SECRETING T-CELLS

CLAIM FOR BENEFIT OF FILING DATE OF PROVISIONAL APPLICATION

This application hereby claims the priority date of the U.S. Provisional Application Ser. No. 60/241,001, filed Oct. 18, 2000, by Brice et al.

BACKGROUND OF THE INVENTION

1. Field of the Invention

Here, we describe a sensitive and specific assay and kit for the detection of chemokines having activity that is upregulated by Th-1 cytokines such as IFN-γ (interferon-γ) and chemokines that upregulate the activity of Th-1 cytokines (such as IFN-γ). The invention also relates to a sensitive and novel immunoassay method and kit for detecting MIG (Monokine Induced by interferon-γ) or other chemokines whose production is upregulated by IFN-γ. Also, the invention relates to a method of assessing the effectiveness of a compound or system in inducing an immune response by detecting the induction of the expression of such a chemokine. All references mentioned in this application are incorporated herein by reference, in their entirety.

2. Description of the Background Art

The ability to assess specific immune responses is critical for understanding the immune mechanisms underlying disease, defining the types of responses to be induced by vaccination, and evaluating vaccine efficacy. Particular emphasis has been placed on the measurement of T cell mediated responses and the identification of immune markers thought to correlate with protection. In this specification and the claims that follow, the term "immune response" includes responses that modify a pre-existing immune response.

Cytokines are immune system proteins that are biological response modifiers. Monokines are chemokines secreted from monocytes. Chemokines are cytokines that have chemoattractant properties. These biological proteins are discussed, for example, in the *Illustrated Dictionary of Immunology*, ed. Cruse, J. M. and Lewis, R. E., CRC Press, N.Y., (1995).

In the present application and the claims that follow, an immunoreactive substance is defined as a substance to which antibodies, or immune cells, (such as T cells and NK cells) can bind, or which stimulates the production of antibodies or activate or induces T cells. That is, an immunoreactive substance can be considered as a compound capable of inducing an immune response. Although immunoreactive substances are typically thought of as whole molecules or organisms, the term "immunoreactive substance" may also be considered as that portion of a molecule or organism which elicits the immune response. For the purposes of the present specification and the claims that follow, two immunoreactive (including antigenic) substances are considered to be the same if they each share at least one common immunoreactive portion.

IFN-γ is a prototypic Th-1 cytokine produced by a variety of cells including CD4[+] T cells, CD8[+] T cells and NK cells (1). The importance of this cytokine in mediating protection against a number of pathogens, including parasites, bacteria, and viruses has been well established (1). IFN-γ has been known to play a central role in orchestrating a range of immunological programs which are critical for immune protection. These programs include induction of genes involved in antigen processing, upregulation of MHC Class I and Class II expression, induction of oxygen and nitrogen radicals, and stimulation of chemokine production in vitro and in vivo (1-5). Thus, in many systems, detection of IFN-γ or IFN-γ secreting cells serves a marker for the biological effects of IFN-γ activity. Accordingly, in many systems, detection of IFN-γ or IFN-γ secreting cells following exposure to antigen is frequently used to determine immunological responsiveness.

Through their ability to recruit distinct populations of leukocytes, chemokines have the ability to enhance antigen-specific immune responses. Since IFN-γ is known to regulate the production of various chemokines (6), we sought to determine if one or more chemokines could be used as a surrogate marker for antigen-specific IFN-γ production. We hypothesized that evaluating the biological effects of IFN-γ production rather than directly quantitating IFN-γ or IFN-γ producing cells per se may provide a more sensitive and reproducible means of detecting antigen-specific IFN-γ activity. Accordingly, we studied a panel of chemokines implicated in IFN-γ mediated immune responses, including Monokine Induced by interferon-γ (MIG), Interferon-γ-inducible Protein-10 (IP-10), Monocyte Chemoattractant Protein-1 (MCP-1), Macrophage Inflammatory Protein-α (MIP-α), and Regulated Upon Activation, Normal T-cell Expressed and Secreted (RANTES) (7, 8). This disclosure describes a novel assay for detecting antigen-specific MIG or antigen-specific IFN-γ or antigen-specific IFN-γ producing T-cells, based on flow cytometric quantitation of the antigen-specific, MHC-restricted, IFN-γ mediated induction of MIG expression. Our studies establish that this is a specific and sensitive assay for detecting high as well as low levels of antigen-specific IFN-γ- and/or antigen-specific IFN-γ secreting T-cells.

To date, the detection of low levels of antigen-specific cellular immune responses has been problematic, particularly in human systems. Antigen-responsive CD4[+] T cells responses are routinely detected by assessment of lymphoproliferative potential or capacity to produce antigen-specific cytokines via ELISA. Antigen-specific CD8[+] T cell responses are generally still evaluated by cytotoxic lysis of target cells or limiting dilution analysis (LDA), as they have been for over 15 years. However, these conventional assays are cumbersome and laborious, require extensive tissue culture and are not sensitive enough to detect low frequencies of antigen-specific cells. Furthermore, they can not be used to evaluate responses associated with cells which may respond to specific antigen by cytokine production, for example, but may not proliferate.

More recently, alternative methods have been developed to detect antigen-specific CD4[+] and CD8[+] T cell mediated immune responses. These assays include enumeration of cytokine producing cells at the single cell level by ELISPOT or by flow cytometry using intracellular cytokine staining techniques, or by directly quantitating peptide-specific clonotypes using tetramer technology.

In certain applications, it is desirable to evaluate the production of specific cytokines produced by antigen-specific cells. Currently, detection of antigen-specific cytokine-producing cells by cytokine-specific ELISPOT assay is gaining widespread acceptance as the most appropriate method available for detecting antigen-specific cellular immune responses. This method determines the number of cells producing a specific cytokine after in vitro culture in the presence of a specific peptide/immunogen and can be used to reproducibly detect low numbers of cytokine producing cells. The sensitivity for detecting low frequencies of responsive cells can be increased with prolonged culture and/or restimulation.

However, prolonged in vitro cultivation and variations of culture conditions may not accurately reflect in vivo immunologically relevant events. Additionally, the laboratory procedure for completion of the ELISPOT assay is time consuming. Furthermore, quantitation of ELISPOT is achieved by subjective manual counting or by computerized counting microscopes which provide an objective and reproducible means of enumerating ELISPOTs, however, the cost of these machines do not make them readily available to most laboratories. Moreover, ELISPOT assays require additional time for coating plates and typically longer culture times and an additional day for development for the assay. Accordingly, there is a need in the art for a sensitive, specific, and relatively faster assay that requires short culture time prior to analysis.

Tetramer staining is more sensitive than traditional methods for detecting antigen-specific cells, but the use of this technique is restricted to well characterized epitopes in association with defined MHC alleles, and requires subsequent culture for functional characterization of tetramer-positive cells.

Flow-based intracellular staining methods provide a technically simple and relatively fast method for identifying antigen-responsive cells; however, it is difficult to detect low numbers of antigen-specific cytokine-producing cells at levels significantly above background. The limitation of the assay lies in the fact that low frequency of cytokine producing cells may be indistinguishable above background levels. Addition of immune enhancer reagents, such as antibodies to CD28, are frequently used to augment costimulation in culture conditions but these reagents may bias the results. Success with intracellular staining assays have been most frequently reported in studies evaluating CD4+ T cell responses to viral antigens using PBMC from chronically infected individuals (for example, CMV or HIV). Very limited success has been reported for the detection of ex vivo antigen-specific cells in CD4+ or CD8+ T cells from immunized individuals where the number of circulating antigen-specific cells may be considerably lower than that found in individuals exposed to the infectious agent. Indeed, without using tetramers to select a subpopulation of specific cells for evaluation, it has not been possible to detect low frequencies of antigen-specific cells using flow cytometry for intracellular cytokines. Thus, there is a need in the art for a flow cytometric method of detection low levels of antigen-specific cells with readily available reagents.

In the assays described above, antigen-specific IFN-γ-immune responsiveness is evaluated directly by detecting IFN-γ or IFN-γ producing cells; these assays do not measure the biological response of IFN-γ production from antigen-specific cells as is possible through the amplification effect of MIG. This results in an inability of IFN-γ ELISPOT assays and other detection methods to detect antigen-specific IFN-γ responses at low levels. Accordingly, there is a need in the art for a very sensitive assay for quantitative measure of IFN-γ activity or for detecting antigen-specific IFN-γ-producing cells.

Farber et al., WO 92/10582, published Jun. 25, 1992, teach methods for producing MIG proteins, nucleotide sequences, probes, and antibodies. In a single sentence in the embodiment, the authors implicate that detection of MIG may potentially be used to bioassay for IFN-γ. It is suggested that a sample containing an unknown quantity of IFN-γ is applied to a macrophage or monocytic cell line and the amount of MIG proteins, or MIG messenger RNA which is made in response to the applied IFN-γ may be subsequently quantified. Quantification is taught to be possible by any means known in the art, such as radioimmunoassay, Northern blots, Western blots, enzyme-linked immunoadsorbent assay, etc. The amount of the MIG protein or mRNA produced by the cells in response to the applied IFN-γ would potentially correlate with the amount of IFN-γ in the sample (but no evidence is presented). See WO 92/10582 at pp. 8-9. There are no embodiments in the PCT for using MIG as a bioassay for IFN-γ. More, specifically, there are no embodiments described using the detection of MIG as a marker of antigen-specific immune responsiveness, or antigen-specific IFN-γ production. Moreover, there is no description of how MIG expression could be used as a marker for detecting antigen-specific cells or for detecting antigen-specific IFN-γ producing cells. Thus, there is a need in the art for a more sensitive assay that uses the induction of MIG expression as a marker for antigen specific IFN-γ producing cells or antigen-specific IFN-γ production. While Farber implicates the use MIG as a bioassay for IFN-γ, our application describes induction of MIG expression as a marker for immune responsiveness.

Amichay et al. 1996 (Genes for chemokines HuMig and Crg-2 are induced in protozoan and viral infections in response to IFN-γ with patterns of tissue expression that suggest nonredundant role in vivo. J. Immunol. 157:4511) teach in vivo MIG expression following exposure to a pathogen. In that report, mice were experimentally infected with protozoan or viral pathogens and the level of MIG expression was assessed. Compared to non-exposed controls, induction of MIG expression was noted in various organs and tissues in response to infection, demonstrating that MIG expression is induced following in-vivo infection. Specifically, Amichay demonstrated that infection of mice with different pathogens induced expression of MIG in various organs. Induction of MIG expression following in vivo infection was not observed if they used IFN-γ knockout mice (mice that are genetically incapable of producing IFN-γ). Similarly, injecting mice with IFN-γ also induced MIG expression in various organs as well. These studies did not demonstrate that induction of MIG expression was antigen-specific or genetically-restricted or general to inflammatory stimuli induced by infection, or if it was a consequence of IFN-γ production from antigen-specific cells or if production was specifically mediated by CD8+ T cells, CD4+ T cells, and/or NK cells. Accordingly, there is a need in the art to develop a sensitive and specific assay for IFN-γ activity or other Th-1 cytokine which is based on the detection of MIG or other chemokine as a marker for antigen-specific immune responsiveness or for detecting antigen specific IFN-γ cells.

Recent studies have implicated MIG as an important immune effector molecule in its own right. Like IP-10 and I-TAC, MIG binds to a common receptor, CXCR3, which is known to be expressed on the surface of activated/memory T cells and NK cells (28). These chemokines are induced by a variety of cell types in response to IFN-γ (23, 29, 30). MIG has been shown to enhance NK cell mediated cytotoxicity and to mediate antitumor and antiviral responses in vivo (31, 32). Neutralization of MIG has also been shown to prolong graft survival in vivo (33). Since expression of MIG mRNA can be detected in a variety of different organs following IFN-γ administration, including liver, thymus, lung and spleen, or in the liver and spleen of mice following infection by *P. yoelli* or *T. gondii* (7), it is likely that MIG may represent a key mediator of protective immunity.

SUMMARY OF THE INVENTION

The evaluation of antigen-specific immune responses is critical for understanding the mechanisms of immune protection, for establishing the efficacy of candidate vaccines, and for diagnostics. Here, we describe a sensitive and specific assay for detecting antigen-specific MIG expression and/or antigen-specific IFN-γ activity which is based on the detection of the chemokine monokine induced by gamma interferon (MIG) as a measure of the biological effect of IFN-γ, rather than direct quantitation of IFN-γ or IFN-γ secreting cells per se. In laboratory studies, upregulation of MIG expression was observed following in vitro activation of PBMC with defined $CD8^+$ T cell epitopes derived from influenza virus (FLU), CMV, or EBV, and in all cases induction of MIG expression was antigen-specific, genetically restricted and dependent on both $CD8^+$ T cells and IFN-γ. Further, antigen-specific MIG expression was also demonstrated in an experimental vaccine model using volunteers immunized against malaria. Responses as assessed by the MIG assay paralleled those detected by conventional IFN-γ ELISPOT, but the magnitude of response and sensitivity of the MIG assay were superior. This was demonstrated by the ability of the MIG assay to detect antigen-specific immune responses that were not detectable as positive results using the IFN-γ ELISPOT assay, and by depletion-reconstitution studies which demonstrated that the sensitivity of the MIG assay could be least twice as sensitive than the ELISPOT assay for detecting positive responses. Further demonstration of the sensitivity of detecting induction of MIG expression compared to IFN-γ responses is also provided by detection of MIG protein, but not IFN-γ, by ELISA using cell culture supernatant. Our data validate this novel method for the detection of low levels of antigen-specific and genetically restricted IFN-γ activity.

OBJECTS OF THE INVENTION

Accordingly, an object of this invention is a rapid immunodiagnostic assay method for detecting antigen-specific MIG expression or antigen-specific IFN-γ production or IFN-γ producing cells by detecting MIG expression.

Another object of this invention is a method of assessing the effectiveness of a compound or system in inducing an immune response by detecting the amount of MIG expression.

Still another object of this invention is the detection of low levels of IFN-γ through detecting MIG expression.

Yet another object of this invention is a method of assessing antigen-specific immune responsiveness through the detection of MIG expression.

Another object of this invention is an immunoassay method for detection of MIG expression during $CD8^+$ deletion and add-back experiments.

A further object of the invention is an immunoassay kit for detecting IFN-γ or IFN-γ secreting cells.

A yet further object of the present invention is the detection of CD8 IFN-γ-producing cells or $CD8^+$ T cell-mediated IFN-γ product.

A still further object of the present invention is the detection of CD4 IFN-γ-producing cells.

A yet additional object of the present invention is the detection of $CD8^+/CD4^+$ IFN-γ-producing cells.

A still additional object of the present invention is the detection of cytokines that upregulate the production of MIG or the detection of cytokines whose production is upregulated by IFN-γ.

These and additional objects of the invention are accomplished by a detection method and kit which is based, at least in part, on the biological amplification of Th-1 cytokine responses, thus providing a sensitive means for detecting high as well as low levels of antigen-specific Th-1 cytokine or antigen-specific Th-1 cytokine producing cells and a means for assessing the effectiveness of compounds or systems in inducing an immune response.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

FIG. 1 is a representation of the antigen-specific induction of MIG expression mediated by IFN-γ.

FIG. 2 is a representation of an example MIG assay and method.

FIG. 3 is a graph of the induction of chemokine expression by IFN-γ.

FIG. 4 is flow cytometry data showing the antigen-specific and genetically restricted induction of MIG expression.

FIG. 5 is a bar graph showing that MIG expression is dependent on IFN-γ.

FIG. 6 is a bar graph showing the kinetics of antigen-specific induction of MIG expression.

FIG. 7 is a bar graph showing the implicated cellular mechanism of antigen-specific induction of MIG expression.

FIG. 8 is a bar graph showing the effect of selective $CD8^+$ T cell enrichment on the antigen-specific induction of MIG expression.

FIG. 9 is a bar graph showing the antigen-specific induction of MIG expression in an example vaccine model.

FIG. 10 is a bar graph that demonstrates the ability to detect antigen-specific induction of MIG expression using whole blood stimulation protocols.

DESCRIPTION OF THE PREFERRED EMBODIMENTS

This invention is directed to an immunodiagnostic assay and method to detect cytokines that upregulate the production of IFN-γ, or to detect cytokines whose production is upregulated by MIG. Typically, the invention includes an immunodiagnostic assay and method to detect MIG or to detect IFN-γ or IFN-γ secreting cells by assessing the amount of MIG expression. The vertebrate immune system is a complex system that is comprised of various organs, tissues, cells and cells products that provide protection against pathogenic organisms, toxins, or neoplastic cells. The immune system can be further divided into the innate immune system and the acquired immune system. The focus of this patent will be on the acquired immune system, specifically cellular immune responses which are mediated by at least three functionally distinct classes of cells: $CD4^+$ T cells, $CD8^+$ T cells, and NK cells. Activation of these cells is mediated in part by the recognition of antigenic peptide fragments that are presented in conjunction with major histocompatibility molecules (MHC). Through receptors on the cell surface, $CD4^+$ T cells recognize peptides presented by MHC class II molecules, while $CD8^+$ T cells recognize peptides presented by MHC class I molecules. The MHC complex is considered the most polymorphic region of the human genome and consists of at least 200-1000 different genes which may express 8-10 different alleles. Both MHC class I and class II molecules contain a groove within their structure which allows for binding of peptides which fit precisely into a specific MHC haplotype. T cells and NK cells express a distinct receptor on their cell surface which can recognize a specific antigen/MHC complex. The interaction of these cell surface molecules mediates the specificity of the immune response. Thus, a given T cell or NK cell is only activated by recognition of a specific and distinct antigen/MHC complex, and the binding of an irrelevant peptide into the MHC binding groove will not activate those specific cells. Thus, antigen-specific immune responses refers to the ability of the immune system to distinguish a specific antigen/MHC complex from one another. The response is said to be genetically-restricted if expression of the antigenic peptide is restricted to a given MHC haplotype.

For instance, if a cell in the body were to be infected with a virus, antigens encoded by the virus could be expressed on the surface of the infected cells in conjunction with MHC molecules. T cells and NK cells are to recognize the antigen/MHC complex and are activated to eliminate the infection. Elimination of infection could be achieved by a variety of different measures, including lysis of infected cells by CTLs and NK cells or through the production of cytokines which may in turn activate protective pathways inside the infected cell, or prevent infection from spreading to neighboring cells.

The invention described herein teaches a new method for detecting the presence of antigen-specific cytokine (e.g. IFN-γ)-producing cells through the detection of an effect of its activity, the induction of the expression of a second cytokine, e.g., MIG. As mentioned above, cytokines such as IFN-γ mediates a variety of biological responses, one such response is the induction of chemokines, such as MIG. Both MIG and IP-10 are two chemokines belonging to the α superfamily of chemokines that are known to be induced following exposure to recombinant IFN-γ. However, it is known that IP-10 can be induced by factors other than IFN-γ including IFN-α, IFN-β, and LPS while MIG expression is not induced by these factors. The proposed model for antigen-specific induction of MIG expression mediated by IFN-γ is shown in FIG. 1. An antigen-presenting cell (APC) expresses a specific antigen-MHC class I complex on its cell surface for recognition by immune cells, namely $CD8^+$ T cells, or NK cells. This antigen-specific, genetically-restricted interaction activates immune cells to produce IFN-γ. Production of IFN-γ induces the expression of MIG in the cognate APC, as well as neighboring APC. Thus, detecting MIG expression is the result of biological amplification of IFN-γ production and provides a specific and sensitive means of detecting low levels of IFN-γ activity and IFN-γ producing cells, or other Th-1-type cytokine-producing cells. This is a unique feature for detecting antigen-specific IFN-γ producing cells through the detection of MIG expression by flow cytometry or other means known by those skilled in the art. Such means include but are not limited to RIA, ELISA, ELISPOT, RT PCR, and flow-based assays, and bead-based assays. In a flow based assay, the sample is detected (e.g., by fluorescence or other means) while flowing through detection windows. Flow-based assays include, e.g., flow cytometry. In a bead-based assay, a fluorescent bead is covalently attached to a detecting antibody. A bead-based assay can be analyzed by any flow cytometry or any device or method that can quantitatively detect fluorescent beads. Detection of antigen-specific cells by flow cytometry offers many advantages over more conventional assays.

ADVANTAGES AND NEW FEATURES

In addition to sensitivity, the instant assay has a number of additional advantages over other assays. For example, antigen-specific IFN-γ restricted responses can be readily detectable by MIG assay following a few hours of incubation with antigen. In the examples provided herein, antigen-specific induction of MIG expression was detectable following 4-16 hours of culture. In contrast, those of skill in the art frequently utilize longer culture time for the ELISPOT assay (24-36 hours and as long as 13 days). Additionally, even if the variable culture time is discounted from each method the MIG assay is at least 2.85 times faster to perform from start to finish than the ELISPOT assay which is comparable to other current detection methods. (Table IV). Thus, the MIG assay also provides a method for detecting antigen specific IFN-γ responses that is less laborious and requires less time to complete and evaluate.

Furthermore, because the assay of the present invention can be a flow cytometry-based assay, it can be technically simple and a relatively rapid and objective method for identifying antigen-specific cells. However, current protocols for detecting antigen-specific cytokine producing cells by intracellular staining and flow cytometry do not provide a robust means of reproducibly detecting low levels of antigen-specific, cytokine producing cells at significant levels above background. Because antigen-specific induction of MIG expression is the result of biological amplification of IFN-γ responses, it provides a novel alternative for detecting low levels of antigen-specific, IFN-γ restricted responses by flow cytometry and a measure of immune responsiveness. Detection of MIG expression by flow cytometry evaluates the frequency of responsive cells and magnitude of response at a large-scale, single cell level, as compared with the ELISPOT assay where it is the number of responsive cells in a limited sample in each well that are detected and enumerated. Antigen-specific detection of MIG expression by flow cytometry is more sensitive than the IFN-γ ELISPOT assay because it is based on the biological amplification of IFN-γ responses, allowing the detection of positive responses that are not scored positive by the IFN-γ ELISPOT assay conducted in parallel. As shown in the Examples disclosed herein, the use of $CD8^+$ T cell depletion and add-back experiments provides one example demonstrating that the MIG assay can be at least two times more sensitive than the IFN-γ ELISPOT assay.

In a typical embodiment, the invention uses a new assay for detecting IFN-γ other Th-1 cytokines or cells secreting IFN-γ or other Th-1 cytokines by measuring one of the biological effects of the activity of the cytokine through flow cytometric detection of the chemokine whose production is upregulates. The detection of IFN-γ (or other Th-1 cytokine) or IFN-γ producing (or other Th-1 producing) cells can be done using samples obtained from a variety of bodily fluids, tissues, or cells, including whole blood, plasma, serum, PBMC preparations, saliva, tears, and biopsy samples.

We describe a method for detecting MIG (or a cytokine whose production is upregulated by a Th-1 cytokine) or a Th-1 cytokine (e.g., IFN-γ) or Th-1 cytokine (e.g., IFN-γ) producing cells using peripheral blood mononuclear cells (PBMC's) isolated from whole blood. The general principle of the assay is as follows. A sample is obtained from a host and cultured with an antigen, such as a known pathogen or fragment thereof. Culture of the sample with an antigen serves to activate immune cells to produce the Th-1 cytokine, e.g. IFN-γ. The Th-1 cytokine in turn induces the production of chemokine (e.g., MIG) molecules which are detected by flow cytometry. (FIG. 2). Alternative means for detecting the level of chemokine expression can include, but are not limited to, ELISPOT, RIA RT-PCR, bead-based assays, etc. Detection of chemokine molecules for the purpose of this invention can include MIG DNA, RNA, full-length protein or a peptide thereof.

In another embodiment, the detection of chemokine (e.g., MIG) expression from ex vivo samples can be used to determine if a compound or system is effective in inducing IFN-γ (or other Th-1 cytokine) responses in individuals. Compounds include substances known to enhance immune responses such as adjuvants or systems such as whole organisms, subunits of whole organisms, or vaccine delivery systems. Baseline levels of chemokine (e.g., MIG) expression could be determined in the individual prior to immunization using compounds or novel systems. Following immunization, a sample from the individual could be obtained and chemokine expression detected and compared to baseline levels of that chemokine's expression or to control individuals who were not immunized. Both vaccinated and unvaccinated individuals could also be administered a fragment of the vaccine, and samples obtained from these individuals could be used to assess the level of antigen-specific induction of chemokine expression in immunized and non-immunized individuals as a measure of immune responsiveness.

Additionally, the method can be used to determine the immune status of a mammal, such as a human. Various diseases, such as HIV, and genetic conditions, reduce the immunoresponsiveness of their patients by attacking cells that mediate the expression of MIG or similar cytokine/chemokines whose production is upregulated by IFN-γ or other Th-1 cytokines. Thus, an assay for MIG (or other chemokine) expression can effectively monitor the progress of the disease of the response of a subject to treatment.

In another embodiment, the method could be incorporated into a kit, which may or may not include an antigen, such as a known pathogen or fragment thereof, and other reagents, such as indictors for MIG or for other chemokines whose expression is upregulated by IFN-γ or other Th-1 cytokines. Indicators for MIG and similar chemokines are substances, such as labeled (e.g., fluorescently) antibodies to MIG, that allow the specific detection and quantitation of MIG or the desired chemokine. Typically, indicators for MIG or similar chemokines bind covalently to MIG or the desired chemokine, either by direct attachment or via an intermediate molecule. The kit and assay could be performed by obtaining a sample in a field or laboratory or clinical setting, and the amount of MIG or similar chemokine expression could be determined by various means, e.g., flow cytometry, RIA, ELISPOT, ELISA, RT-PCR, or bead-based assays.

Although the invention has been discussed mainly with respect to MIG and IFN-γ, those skilled in the art will recognize that the detection of MIG expression may be used as a marker for the presence and quantitation of other cytokines whose production it upregulates. Similarly, other cytokines that upregulate the production of IFN-γ or other Th-1 cytokines may be used as a marker for the presence and quantitation of IFN-γ or other cytokines.

Having described the invention, the following examples are given to illustrate specific applications of the invention, including the best mode now known to perform the invention.

EXAMPLE 1

PBMC Samples and Cell Culture

Study subjects were healthy Caucasian volunteers, aged 22-51, who were seronegative for HIV gp120 antibodies and HBV core antibodies, as determined by standard clinical screening. HLA allelic frequencies were established from peripheral blood samples using standard site-specific oligonucleotide PCR typing). PBMC were isolated by standard gradient centrifugation over Ficoll-Paque (Amersham Pharmacia Biotec AB, Uppsala, Sweden). Cells were cultured in RPMI 1640 containing 10 mM Hepes and supplemented with 10% heat-inactivated FCS (Sigma Chemical Co., St. Louis, Mo.), 2 mM L-glutamine, 100 U/ml penicillin, and 100 ug/ml streptomycin (Life Technologies, Grand Island, N.Y.). In some experiments, PBMC were depleted of specific subsets ($CD4^+$, $CD8^+$, $CD16^+$ or $CD56^+$ cells) prior to culture using MACS beads (Miltenyi Biotec, Auburn, Calif.), as described by the manufacturer. Depleted cultures were analyzed by flow cytometry and in all cases the efficiency of depletion was at least 95%. All experiments reported herein were conducted using fresh PBMC. Other studies have established that similar responses can be detected using frozen PBMC (data not shown).

Synthetic Peptides

Synthetic 9-mer or 10-mer peptides representing well characterized HLA-A*0201 restricted epitopes from the influenza matrix protein (FLU, residues 58-66) (9), cytomegalovirus phosphoprotein (CMV, residues 495-503, (10, 11), human immunodeficiency virus gag protein (HIV, residues 75-85) (9), and hepatitis B virus core antigen (HBV, residues 18-27) (12) were purchased from Chiron Corporation (Clayton, VIC, Australia) or Research Genetics (Huntsville, Ala.) and were purified to >95%. Peptides representing HLA-DR restricted $CD4^+$ T cell epitopes and nested HLA-A*0201 restricted $CD8^+$ T cell epitopes from the *P. falciparum* circumsporozoite protein (CSP) (13-19) were obtained from Chiron Corporation. The 9-mer peptide representing the HLA-B8 restricted epitope from the Epstein-Barr virus nuclear antigen 3 (EBV, residues 339-347) (20). Peptide sequences are presented in Table I.

EXAMPLE 2

MIG is Induced in Response to the Expression of IFN-γ

To investigate the profile of chemokines induced following exposure to IFN-γ which could be readily detected by intracellular staining and flow cytometry, PBMC were cultured with recombinant human IFN-γ (rec.hIFN-γ) and stained intracellularly with mAbs to MIG, IP-10, MCP-1, RANTES, or MIP-α. Expression of both MIG and of IP-10 was readily detectable in PBMC following overnight culture (FIG. 3A). MCP-1 and MIP-1α expression were slightly upregulated compared to media control but there was no change in expression of RANTES (data not shown). Additional dose titration experiments demonstrated that MIG expression was a more sensitive measure of IFN-γ as compared to IP-10 (FIG. 3B). Moreover, it has been established that the induction of MIG is restricted to IFN-γ, whereas IP-10 can be induced by factors other than IFN-γ including IFN-α, IFN-β, and LPS (22-24). Therefore, expression of MIG, but not IP-10, can be considered a surrogate marker of IFN-γ specific activity, and subsequent studies focused on the induction MIG expression.

EXAMPLE 3

Induction of MIG Expression is Antigen-Specific and Genetically Restricted

We evaluated whether MIG expression could be induced in an antigen-specific and genetically restricted manner. PMBC from volunteers known to express HLA-A*0201 were cultured with peptides containing HLA-A*0201-binding $CD8^+$ T cell epitopes derived from HIV, HBV, FLU and CMV.

Representative flow cytometric data from one experiment is presented in FIG. 4. MIG expression was detected with PBMC from HLA-A*0201-positive volunteers (Vols. #1, 2 and 3) activated with CMV and FLU peptides, but not HIV or HBV peptides indicating that the response was antigen-specific. Additionally, antigen-specific induction of MIG expression was not detected in cultures from volunteers who did not express the HLA-A*0201 allele (Vols. #15 and #16) demonstrating that the antigen-specific response was genetically restricted. These data established that culture of PBMC with synthetic peptides elicited antigen-specific and genetically-restricted MIG expression,

EXAMPLE 4

Induction of MIG Expression is IFN-γ Dependent

Having established that rec.hIFN-γ induced MIG expression and that culture of PBMC with synthetic peptides elicited antigen-specific and genetically-restricted MIG expression, we determined whether the induction of MIG expression was dependent on IFN-γ. Accordingly, PBMC were cultured with FLU or CMV peptide in the presence or absence of neutralizing mAbs to IFN-γ or a control mAb (mIgG). Analysis of means and standard deviation of quadruplicate culture and staining wells is shown in FIG. 5. In two volunteers, the addition of neutralizing mAbs to IFN-γ inhibited antigen-specific induction of MIG expression by an average of 87% and 85% to the FLU and CMV peptides, respectively. In repeated experiments with PBMC from volunteers 1-3, the addition of neutralizing antibodies to IFN-γ inhibited antigen-specific induction of MIG expression to both FLU and CMV peptides by 86%, indicating that antigen-specific induction of MIG expression was dependent upon IFN-γ.

EXAMPLE 5

Kinetics of Antigen-Specific Induction of MIG Expression

Since IFN-γ is rapidly produced by T cells following exposure to antigen, we evaluated the kinetics of antigen-specific induction of MIG expression. Antigen-specific induction of MIG expression was found to be rapidly induced in PBMC cultured with CMV and EBV peptides and was readily detectable after 4 hours of culture (FIGS. 6A and B). These results demonstrate that the antigen-specific induction of MIG expression is rapid (within 4 hours) and is sustained for at least 16 hours, at least for these peptides. Early kinetic experiments were also conducted with the FLU peptide (FIG. 6C). With this peptide, antigen-specific induction of MIG expression was detected in one of two volunteer after 4 hours of culture (Vol. #5), but increased with additional time and was readily detectable in both volunteers following 6 hours of culture (FIG. 6C). In these cultures, the rapid induction of MIG expression was shown to be dependent upon IFN-γ from activated cells, as the addition of neutralizing antibodies to IFN-γ inhibited the antigen-specific induction of MIG expression. Antigen-specific IFN-γ responses could also be detected by ELISPOT at similar time points (data not shown), and studies are underway to more precisely define the early kinetics of response for both MIG and ELISPOT assays.

EXAMPLE 6

Cellular Requirements for Optimal Antigen-Specific Induction of MIG Expression

The HIV, HBV, CMV, FLU and EBV peptides used in these studies were 9-mers or 10-mers known to be restricted by the HLA-A*0201 or HLA-B8 Class I molecules. Therefore, we reasoned that the antigen-specific, MHC-restricted induction of MIG expression was mediated by $CD8^+$ T cells following recognition of the peptide/MHC complex on the surface of the APC. To test this, PBMC were depleted of $CD8^+$ T cells ($CD8^-$). In all cases, depletion of $CD8^+$ T cells significantly inhibited the antigen-specific induction of MIG expression, demonstrating that $CD8^+$ T cells were mediating the antigen-specific response. The analysis with means and standard deviation of quadruplicate wells is presented in FIG. 7. The dependence on $CD8^+$ T cells for MIG expression was confirmed in subsequent selective enrichment studies where the induction of MIG expression from $CD8^+$ T cell depleted cultures could be reconstituted by the addition of $CD8^+$ T cells.

Both $CD4^+$ T cells and NK cells are known to be major producers of IFN-γ (1). In addition, $CD56^+$ and $CD16^+$ are considered prototypic markers for NK cells, although a recent study suggests that CD56 may also represent a marker for $CD8^+$ effector T cells (25). Accordingly, to investigate the role for these cells in the induction of MIG expression, we specifically depleted PBMC cultures of $CD4^+$, $CD56^+$ or $CD16^+$ cells. As shown in FIG. 7 depletion of $CD4^+$ T cells or $CD56^+$ cells (or $CD16^+$ cells; data not shown) did not inhibit the robust expression of MIG in cultures activated with either the CMV or EBV peptides. However, depletion of $CD4^+$ T cells or $CD56^+$ cells (or CD $16^+$ cells; data not shown) did decrease the more modest induction of MIG expression in cultures activated with the FLU peptide.

Requirements for IL-12 and IL-2 for Bystander Induction of MIG Expression

Both IL-2 and IL-12 are known to induce IFN-γ production by $CD4^+$ T cells and NK cells (26). Therefore, to investigate if IL-2 and IL-12 were involved in bystander activation, neutralizing mAbs to IL-12 or to CD122 were added to cultures activated with the FLU, CMV or EBV peptides. CD122 (IL-2Rα) is part of the IL-2 receptor complex and antibodies to this component are known to block the binding of IL-2 (27). As shown in FIG. 7, addition of neutralizing mAbs against IL-12 or IL-2 had no effect on the response to either the CMV or EBV peptides. However, addition of mAbs to IL-12 and CD122 did decrease MIG expression in PBMC cultured with the FLU peptide. These results are consistent with observations from the depletion experiments described above, and suggest that the $CD4^+$ T cells and NK cells required for optimal induction of MIG expression in the FLU system are activated nonspecifically through IL-12 and IL-2 cytokine feedback loops. In contrast, antigen-specific induction of MIG expression to CMV or EBV peptides appears to be dependent on $CD8^+$ T cells but not dependent on bystander activation of $CD4^+$ T cells or NK cells for optimal expression. Furthermore, the requirement for bystander activation appears to be reflected in the magnitude of the antigen-specific MIG response, since a more robust response was observed with the CMV and EBV peptides as compared with the FLU peptide. The magnitude of the antigen-specific induction of MIG expression directly correlated with the frequency of antigen-specific IFN-γ-producing cells as determined by parallel IFN-γ ELISPOT, as shown in Table II.

EXAMPLE 7

Comparison of MIG, MIG-ELISA, and ELISPOT Assays

MIG Assay

PBMC were cultured at a concentration of $0.5 \times 10^6$ cells/well in a total volume of 200 µl complete medium in a 96-well round bottom plate at 37° C., in an atmosphere of 5% $CO_2$. Synthetic peptides were added at a final concentration of 10 µg/ml prior to initiation of culture. Brefeldin-A or monesin were not added to cultures. Unless otherwise indicated, effectors for the MIG assay were cultured overnight (16-20 hours), in triplicate or quadruplicate. Then, PBMC were washed once in cold Dulbecco's PBS, and stained with mAbs to CD14 or CD11a (Becton Dickinson, San Jose Calif.). PBMC were permeabilized with Cytofix/Cytoperm (Pharmingen, San Diego, Calif.) according to manufacturer's instructions, and stained intracellularly with PE-conjugated mAbs to the human chemokines MIG, IP-10, MCP-1, MIP-1α, RANTES, or IFN-γ (Pharmingen) at a concentration of 0.4 µg antibody/$10^6$ cells. Samples were acquired on a Becton Dickinson FACSCAN (San Jose, Calif.). For each analysis, at least 25,000 events were acquired and cells were gated within the monocyte/macrophage population based upon forward scatter (FSC) and side scatter (SSC) characteristics. Gated cells were analyzed for percentage of CD14- or CD11a-positive cells counter-stained with anti-MIG mAb using the CellQuest software (Becton Dickinson).

IFN-γELISPOT Assay

The number of peptide-specific IFN-γ producing cells was determined by ELISPOT assay, basically as described elsewhere (21). In brief, sterile 96-well multiScreen-IP MAIP plates (Millipore, Bedford, Mass.) were coated overnight at 4° C. with 50 µl of PBS containing 10 µg/ml of anti-IFN-γ mAb (clone 1-D1K; Mabtech, Stockholm, Sweden). Wells were washed 6 times with RPMI-1640 and blocked for 1 hour at room temperature with 100 µl of RPMI-1640 supplemented with 10% FCS. Then, 100 µl of input PBMC ($5 \times 10^5$ – $2.5 \times 10^5$ PBMC) were added in quadruplicate, together with 100 µl of test or control peptide at a final concentration of 10 µg/ml. Unless otherwise indicated, cultures were incubated for 36 hours at 37° C. in an atmosphere of 5% $CO_2$. Wells were then washed 6 times with PBS/0.05% Tween 20 (Sigma chemical Co., St. Louis, Mo.), and incubated for 3 hours at room temperature with 100 µl of 1 µg/ml biotinylated anti-IFN-γ mAb (clone 7B6-1, Mabtech). Wells were again washed 6 times with PBS/0.05% Tween 20 and incubated for 1 hour at room temperature with 100 µl of 1:1000 dilution of streptavidin alkaline phosphatase (Mabtech). Wells were washed 6 times with PBS/0.05% Tween 20 and 3 times with PBS, and then developed with 100 µl of 1:25 diluted alkaline phosphatase substrate (Bio-Rad, Hercules, Calif.). The colorimetric reaction was stopped after 15 minutes by extensive washing in tap water and plates were air-dried. The number of spots corresponding to IFN-γ-producing cells in wells (IFN-γ spot forming cells; SFCs) were enumerated with the Zeiss KS ELISPOT system (Carl Zeiss Inc., Thornwood, N.Y.). Responses were expressed as the number of IFN-γ secreting cells (spot-forming colonies, SFCs) per $10^6$ PBMC.

MIG ELISA

Immunolon 2HB 96-well plates (Dynex Technologies, Chantilly, Va.) were coated overnight at 4° C. with 100 µl of PBS containing 2.5 µg/ml of anti-MIG mAb (clone B8-11; Pharmingen). Plates were washed 3 times with PBS/0.05% Tween 20 and blocked for 2 hours at room temperature with 100 µl of PBS supplemented with 1% FCS. Test samples of cell culture supernatant and recombinant human MIG standards (Pharmingen) were then added in 100 µl volumes in duplicate, and cultures were incubated for 2 hours at room temperature. After 3 washes, 100 µl of PBS containing 2 µg/ml of biotinylated anti-MIG mAb (clone B8-6; Pharmingen) was added to each well, and cultures were again incubated for 2 hours at room temperature. Plates were then washed 3 times and 100 µl of HRP-Streptavidin conjugate (1:2000 dilution; Zymed Laboratories, San Francisco, Calif.) was added for 1 hour at room temperature. Plates were washed 3 times and developed with ABTS substrate solution (KPL, Gaithersburg, Md.) according to the manufacturer's protocol. Concentrations were calculated by interpolation from standard curves based on recombinant cytokine dilutions run in parallel on the same plate.

IFN-γELISA

Human IFN-γ ELISA kits were purchased from Endogen (Woburn, Mass.) and used according to manufacturer's instructions. Concentrations were calculated as described above for the MIG ELISA assay. The sensitivity of this IFN-γ ELISA was 2 µg/ml.

Neutralizing Antibody Treatments

Neutralizing mAbs to IFN-γ (clone B27) and IL-12 (clone C8.6), and blocking antibody to CD122 (clone Mik-γ2) or control mAb (clone MOPC-21), were purchased from Pharmingen. In all studies reported herein, mAbs were added at a final concentration of 20 µg/ml at the initiation of culture and maintained throughout the culture period.

Statistical Analysis

The significance of group differences for the MIG and ELISPOT assays was calculated using the Student's t-Test (Microsoft Excel Version 8.0, Microsoft Corporation). Responses were considered positive if the response to test peptide (FLU, CMV, EBV, or CSP) was significantly different ($p<0.05$) as compared with the response to negative control peptides (HIV or HBV) and if the stimulation index (SI=response with test peptide/response with control peptide) was greater than 2.0.

Comparisons

ELISPOT assays are now routinely used to detect and quantitate antigen-specific cytokine-secreting cells. Since our assay for MIG expression represents an indirect measure of IFN-γ production from antigen-specific cells following biological amplification, we next directly compared the MIG and ELISPOT assays in parallel with samples from the same volunteer using the same peptide. These experiments are summarized in Table II. In multiple parallel studies, the level of MIG expression directly correlated with the number of IFN-γ SFCs obtained by ELISPOT ($R^2=0.94$), supporting our hypothesis that MIG represents a surrogate marker for antigen-specific, IFN-γ-producing cells. In all instances where the ELISPOT assay was considered positive, the corresponding sample met the criteria for positivity in the MIG assay. Moreover, in all instances where cultures were considered positive by either assay, a higher stimulation index was noted with the MIG assay as compared with the ELISPOT assay (average at least 3-fold higher). Finally, in three instances (Vols. #3, 4 and 5 in response to FLU), the response as assessed by the MIG assay was significant, but the corresponding response as measured by ELISPOT was not significant.

We cannot definitively exclude the possibility that these latter responses as assessed by the MIG assay represented false positives. However, in both the ELISPOT and the MIG assays, responses were considered positive only if the response to test peptide was significantly different from the response to negative control peptide(s) and if the stimulation index was 2.0. Although the response to the FLU peptide as compared with the negative control peptides in volunteer #4 was significant, the stimulation index was only 1.7, and this response did not meet our criteria for positivity. In addition, in repeated experiments using PBMC volunteers #3, 4 and 5, positive responses were consistently detected with the MIG assay. These data indicate that the positive responses detected by MIG but not ELISPOT assay do not represent false positives. These data further demonstrate the enhanced sensitivity of the MIG assay for detecting antigen-specific, IFN-γ dependent immune responses.

EXAMPLE 8

Enhanced Sensitivity of the MIG Assay, as Compared with Other Assays, for Detecting IFN-γ-Mediated Antigen Specific Immune Responses To further demonstrate the sensitivity of the MIG assay, and to exclude the possibility that the assay was detecting false positives, we directly compared the MIG and ELISPOT assays in selective enrichment studies using PBMC from volunteers known to respond to a given peptide. For these studies, PBMC from known responders were depleted of $CD8^+$ T cells (<1% and <2% $CD8^+$ T cells for Vols. #2 and #10, respectively) and defined numbers of $CD8^+$ T cells were added back to the $CD8^+$ depleted samples and cultured with either FLU or EBV peptides for 16 hours. In all cases, when compared to HIV or media controls, significant responses (black bars) were detected by the MIG assay before they were detected by the ELISPOT assay conducted in parallel (FIG. 8). In volunteer #2, whose PBMC contained 22% $CD8^+$ T cells, positive responses were detected by ELISPOT when 4% $CD8^+$ T cells were added back to the depleted culture. In the MIG assay conducted in parallel with the same sample, however, responses classified as positive could be detected when only 2% $CD8^+$ T cells were added back to depleted cultures. In volunteer #10 whose PBMC contained 10% $CD8^+$ T cells, positive responses were detectable by the ELISPOT when 4% $CD8^+$ T cells were added back, and by the MIG assay when only 1% $CD8^+$ T cells were added back to depleted cultures. Thus, for these volunteers, the MIG assay was 2 to 4 fold more sensitive than the ELISPOT assay for detecting antigen-specific immune responses.

Antigen-specific induction of both MIG and IFN-γ were also evaluated by cytokine specific ELISAs. Cell-free culture supernatants obtained from samples used in the kinetic studies (FIG. 6) were taken following 8 and 16 hours of culture and evaluated for MIG and IFN-γ by ELISA. As summarized in Table III, MIG could not be detected in samples collected following 8 hours of culture, but was readily detectable in culture supernatant following 16 hours of culture with either the CMV and EBV peptides. As detailed earlier, antigen-specific induction of MIG expression could be detected by flow cytometry within 4 hours of culture, highlighting the sensitivity of the flow-based technique (FIG. 6). IFN-γ was not detectable in culture supernatants from either time point.

In summary, these data establish that the MIG assay provides a specific and sensitive means of detecting low levels of IFN-γ activity and further demonstrate that this assay can detect responses that are below the level of sensitivity of both the standard IFN-γ ELISPOT assay and a MIG-based ELISA assay.

EXAMPLE 9

Induction of Antigen-Specific MIG Expression in a Vaccine Model

Volunteers Immunized with Malaria Sporozoites

Therefore, we have established that the MIG assay could also detect responses in a non-viral infectious disease model (All studies reported above were conducted with immunogenic virally derived peptides with PBMC from volunteers naturally exposed to FLU, EBV, or CMV viruses). PBMC from HLA-A*0201-positive volunteers immunized with irradiated *Plasmodium falciparum* sporozoites were cultured with peptides derived from the *P. falciparum* circumsporozoite antigen (CSP). PBMC from an HLA-A*0201 volunteer who was mock-immunized with noninfected mosquitoes were also cultured with peptides as a control. As shown in FIG. 9, although responses could not be detected to the short malaria peptides (CSP201, CSP202 and CSP203), antigen-specific induction of MIG expression was observed in both immunized volunteers following culture with the longer malaria peptide CSP238. Responses to the second peptide, CSP239, were also detected in one of the two volunteers. Antigen-specific responses to malaria peptides could not be detected in PBMC from the mock-immunized volunteer. These results demonstrate that the MIG assay is able to detect antigen-specific responses induced by immunization.

TABLE IV

Experimental Design of MIG assay compared to ELISPOT Assay

| MIG | | | ELISPOT | |
|---|---|---|---|---|
| | | | Coat plates with antibodies | 2 hours-16 hrs |
| Plate samples with antigen | 1 hr | | Wash plate 9× | .32 hr |
| Incubate samples | variable | | Block plates | 1 hr |
| Centrifuge | .16 hr | | Plate samples | 1 hr |
| Stain | .32 hr | | Incubate samples | variable |
| Wash 2× | .32 hr | | Wash 6× | .32 hr |
| Fix/Perm | .32 hr | | Add biotin | 4 hrs |
| Wash 2× | .32 hr | | Wash 9× | .32 hr |
| Stain | .32 hr | | Add Strep/Avidin | 1 hr |
| Wash 3× | .32 hr | | Wash 9× | .32 hr |
| | | | Add Developing solution | .5 hr |
| Total Time: | 3.08 hrs | | | 8.78-24.78 hrs |

8.78 hrs ÷ 3.08 hrs = 2.85

EXAMPLE 10

Induction of Antigen-Specific MIG Expression Using Whole Blood Stimulation Protocols The previous examples have demonstrated the ability to detect antigen-specific induction of MIG expression using PBMC isolated from whole blood by gradient centrifugation. This process is both laborious and time consuming, and probably involves loss of cells during the processing of the samples. As shown in FIG. 10, antigen-specific induction of MIG expression was readily detectable when whole blood samples were incubated with the listed peptides, demonstrating the feasibility of using unprocessed blood samples for detecting antigen-specific IGN-γ-mediated immune responses. These results also demonstrate the frequency of IFN-γ producing cells determined in parallel samples and highlight the potential for a higher magnitude of response as determined by detecting MIG due to the biological amplification of the IFN-γ response.

Whole Blood Stimulation Protocols

Peripheral blood samples were collected into heparinized vacutainer tubes (Becton & Dickinson, San Diego, Calif.) and 1 ml of blood was aliquoted into round bottom, 15 ml polypropylene tubes. Peptides (20 μg/ml were added to each culture and samples were incubated for 6 hours. After incubation of whole blood with peptides, samples were treated with 2 mM of EDTA for 15 min at room temperature. Erythrocytes were lysed and leukocytes fixed for 10 min at room temperature by adding 10 mls of FACS Lysing solution (Becton & Dickinson). Tubes were washed twice and then cells were permeabilized with FACES Permabilization solution (Becton & Dickinson) prior to staining with antibodies to CD14 and MIG.

REFERENCES

1. Boehm, U., T. Klamp, M. Groot, and J. C. Howard. 1997. Cellular responses to interferongamma. *Annu Rev Immunol* 15:749.
2. Doolan, D. L., and S. L. Hoffman. 1999. IL-12 and NK cells are required for antigen-specific adaptive immunity against malaria initiated by $CD8^+$ T cells in the *Plasmodium yoelii* model. *J. Immunol.* 163:884.
3. Good, M. F., and D. L. Doolan. 1999. Immune effector mechanisms in malaria. *Curr Opin Immunol* 11:412.
4. Sher, A., and R. L. Coffman. 1992. Regulation of immunity to parasites by T cells and T cell-derived cytokines. *Annu Rev Immunol* 10:385.
5. Jouanguy, E., R. Doffinger, S. Dupuis, A. Pallier, F. Altare, and J. L. Casanova. 1999. IL-12 and IFN-gamma in host defense against mycobacteria and salmonella in mice and men. *Curr Opin Immunol* 11:346.
6. Baggiolini, M., B. Dewald, and B. Moser. 1997. Human chemokines: an update. *Annu Rev Immunol* 15:675.
7. Amichay, D., R. T. Gazzinelli, G. Karupiah, T. R. Moench, A. Sher, and J. M. Farber. 1996. Genes for chemokines HuMIG and Crg-2 are induced in protozoan and viral infections in response to IFN-gamma with patterns of tissue expression that suggest nonredundant roles in vivo. *J Immunol* 157:4511.
8. Schrum, S., P. Probst, B. Fleischer, and P. F. Zipfel. 1996. Synthesis of the CC-chemokines MIP-1alpha, MIP-1beta, and RANTES is associated with a type 1 immune response. *J Immunol* 157:3598.
9. Parker, K. C., M. A. Bednarek, L. K. Hull, U. Utz, B. Cunningham, H. J. Zweerink, W. E. Biddison, and J. E. Coligan. 1992. Sequence motifs important for peptide binding to the human MHC class I molecule, HLA-A2. *J Immunol* 149:3580.
10. Parker, K. C., M. A. Bednarek, and J. E. Coligan. 1994. Scheme for ranking potential HLA-A2 binding peptides based on independent binding of individual peptide side-chains. *J Immunol* 152:163.
11. Kern, F., I. P. Surel, C. Brock, B. Freistedt, H. Radtke, A. Scheffold, R. Blasczyk, P. Reinke, J. Schneider-Mergener, A. Radbruch, P. Walden, and H. D. Volk. 1998. T-cell epitope mapping by flow cytometry. *Nat Med* 4:975.
12. Bertoletti, A., F. V. Chisari, A. Penna, S. Guilhot, L. Galati, G. Missale, P. Fowler, H. J. Schlicht, A. Vitiello, R. C. Chesnut, and et al. 1993. Definition of a minimal optimal cytotoxic T-cell epitope within the hepatitis B virus nucleocapsid protein. *J Virol* 67:2376.
13. Calvo-Calle, J. M., J. Hammer, F. Sinigaglia, P. Clavijo, Z. R. Moya-Castro, and E. H. Nardin. 1997. Binding of malaria T cell epitopes to DR and DQ molecules in vitro correlates with immunogenicity in vivo: identification of a universal T cell epitope in the *Plasmodium falciparum* circumsporozoite protein. *J Immunol* 159:1362.
14. Doolan, D. L., S. L. Hoffman, S. Southwood, P. A. Wentworth, J. Sidney, R. W. Chesnut, E. Keogh, E. Appella, T. B. Nutman, A. A. Lal, D. M. Gordon, A. Oloo, and A. Sette. 1997. Degenerate cytotoxic T cell epitopes from *P. falciparum* restricted by multiple HLA-A and HLA-B supertype alleles. *Immunity* 7:97.
15. Good, M. F., D. Pombo, I. A. Quakyi, E. M. Riley, R. A. Houghten, A. Menon, D. W. Alling, J. A. Berzofsky, and L. H. Miller. 1987. Human T-cell recognition of the circumsporozoite protein of *Plasmodium falciparum*: Immunodominant T-cell domains map to the polymorphic regions of the molecule. *Proc. Natl. Acad. Sci. USA* 85:1199.
16. Moreno, A., P. Clavijo, R. Edelman, J. Davis, M. Sztein, F. Sinigaglia, and E. Nardin. 1993. $CD4^+$ T cell clones obtained from *Plasmodium falciparum* sporozoite-immunized volunteers recognize polymorphic sequences of the circumsporozoite protein. *J. Immunol.* 151:489.
17. Moreno, A., P. Clavijo, R. Edelman, J. Davis, M. Sztein, D. Herrington, and E. Nardin. 1991. Cytotoxic $CD4^+$ T cells from a sporozoite-immunized volunteer recognize the Plasmodium falciparum CS protein. *Int. Immunol.* 3:997.
18. Zevering, Y., R. A. Houghten, I. H. Frazer, and M. F. Good. 1990. Major population differences in T cell response to a malaria sporozoite vaccine candidate. *Int. Immunol.* 2:945.
19. Wang, R., D. L. Doolan, T. P. Le, R. C. Hedstrom, K. M. Coonan, Y. Charoenvit, T. R. Jones, P. Hobart, M. Margalith, J. Ng, W. R. Weiss, M. Sedegah, C. de Taisne, J. A. Norman, and S. L. Hoffman. 1998. Induction of antigen-specific cytotoxic T lymphocytes in humans by a malaria DNA vaccine. *Science* 282:476.
20. Burrows, S. R., J. Gardner, R. Khanna, T. Steward, D. J. Moss, S. Rodda, and A. Suhrbier. 1994. Five new cytotoxic T cell epitopes identified within Epstein-Barr virus nuclear antigen 3. *J Gen Virol* 75:2489.
21. Lalvani, A., R. Brookes, S. Hambleton, W. J. Britton, A. V. Hill, and A. J. McMichael. 1997. Rapid effector function in $CD8^+$ memory T cells. *J Exp Med* 186:859.
22. Farber, J. M. 1990. A macrophage mRNA selectively induced by gamma-interferon encodes a member of the platelet factor 4 family of cytokines. *Proc Natl Acad Sci USA* 87:5238.
23. Farber, J. M. 1992. A collection of mRNA species that are inducible in the RAW 264.7 mouse macrophage cell line by gamma interferon and other agents. *Mol Cell Biol* 12:1535.
24. Vanguri, P., and J. M. Farber. 1990. Identification of CRG-2. An interferon-inducible mRNA predicted to encode a murine monokine. *J Biol Chem* 265:15049.
25. Pittet, M. J., D. E. Speiser, D. Valmori, J. C. Cerottini, and P. Romero. 2000. Cutting edge: cytolytic effector function in human circulating $CD8^+$ T cells closely correlates with CD56 surface expression. *J Immunol* 164:1148.
26. Kobayashi, M., L. Fitz, M. Ryan, R. M. Hewick, S. C. Clark, S. Chan, R. Loudon, F. Sherman, B. Perussia, and G. Trinchieri. 1989. Identification and purification of natural killer cell stimulatory factor (NKSF), a cytokine with multiple biologic effects on human lymphocytes. *J Exp Med* 170:827.

27. Tsudo, M., F. Kitamura, and M. Miyasaka. 1989. Characterization of the interleukin 2 receptor beta chain using three distinct monoclonal antibodies. *Proc Natl Acad Sci USA* 86:1982.
28. Loetscher, M., B. Gerber, P. Loetscher, S. A. Jones, L. Piali, I. Clark-Lewis, M. Baggiolini, and B. Moser. 1996. Chemokine receptor specific for IP10 and mig: structure, function, and expression in activated T-lymphocytes [see comments]. *J Exp Med* 184:963.
29. Farber, J. M. 1993. HuMIG: a new human member of the chemokine family of cytokines. *Biochem Biophys Res Commun* 192:223.
30. Luster, A. D., J. C. Unkeless, and J. V. Ravetch. 1985. Gamma-interferon transcriptionally regulates an early-response gene containing homology to platelet proteins. *Nature* 315:672.
31. Mahalingam, S., J. M. Farber, and G. Karupiah. 1999. The interferon-inducible chemokines MuMIG and Crg-2 exhibit antiviral activity in vivo. *J Virol* 73:1479.
32. Kanegane, C., C. Sgadari, H. Kanegane, J. Teruya-Feldstein, L. Yao, G. Gupta, J. M. Farber, F. Liao, L. Liu, and G. Tosato. 1998. Contribution of the CXC chemokines IP-10 and Mig to the antitumor effects of IL-12. *J Leukoc Biol* 64:384.
33. Koga, S., M. B. Auerbach, T. M. Engeman, A. C. Novick, H. Toma, and R. L. Fairchild. 1999. T cell infiltration into class II MHC-disparate allografts and acute rejection is dependent on the IFN-gamma-induced chemokine Mig. *J Immunol* 163:4878.

What is claimed is:

1. An immunoassay method for detecting, a Th-1 cytokine that induces MIG expression, or cells which secrete said cytokine that induces MIG expression, comprising:
    a. obtaining a tissue sample from a mammalian host which has been exposed to an antigen;
    b. culturing said tissue sample in the presence of said antigen;
    c. detecting MIG expression in said sample; and
    d. correlating said detection to the presence of said cytokine which induces said MIG expression or cells that secrete said cytokine that induces said MIG expression in a response to said antigen.
2. The method of claim 1, wherein said mammalian host is selected from the group consisting of a human, a non-human primate, murine, porcine, and bovine.
3. The method of claim 1, wherein said tissue sample is mononuclear cells or whole blood.
4. The method of claim 1, wherein said cytokine is IFN-γ.
5. The method of claim 1, wherein said exposure is selected from the group consisting of natural, experimental, in vivo, and in vitro.
6. The method of claim 1, wherein said MIG expression is amplified due to the production of IFN-γ.
7. The method of claim 1, wherein said MIG expression is medicated by IFN-γ, $CD8^+$ T cells, $CD4^+$ T cells, NK cells.
8. The method of claim 1, wherein said detection is accomplished by the method selected from the group consisting of ELISPOT, flow based system, flow cytometry, bead-based assay, RT/PCR, and ELISA.
9. The method of claim 1, wherein said tissue sample is cultured for less than 20 hours.
10. The method of claim 9, wherein said tissue sample cultured for 4-16 hours before said detecting step.
11. The method of claim 10, wherein said tissue sample is cultured for 16-20 hours.
12. The method of claim 1, wherein said sample includes peripheral blood mononuclear cells isolated from blood drawn from a human subject.
13. An immunoassay method for detecting a Th-1 cytokine that induces MIG expression, or cells which secrete said cytokine that induces MIG expression, comprising:
    a. obtaining a biological sample from a mammalian host which has been exposed to an antigen;
    b. detecting MIG expression in said sample; and
    c. correlating said detection to the presence in said sample of said cytokine which induces said MIG expression or cells that secrete said cytokine that induces said MIG expression in a response to said antigen.
14. The method of claim 13, wherein said biological sample is plasma, serum, tears, nasal secretions, or saliva.
15. The method of claim 13, wherein said mammalian host is selected from the group consisting of a human, non-human primate, murine, porcine, and bovine.
16. The method of claim 13, wherein said tissue sample includes mononuclear cells or whole blood.
17. The method of claim 13, wherein said cytokine is IFN-γ.
18. The method of claim 13, wherein said exposure is selected from the group consisting of natural, experimental, in vivo and in vitro.
19. The method of claim 13, wherein said MIG expression is mediated by IFN-γ, $CD8^+$ T cells, $CD4^+$ T cells, or NK cells.
20. The method of claim 13, wherein said detection is accomplished by the method selected from the group consisting of ELISPOT, flow-based system, flow cytometry, bead-based assay, RT/PCR, and ELISA.
21. An immunoassay for detecting a Th-1 cytokine which upregulates the production of MIG and which is produced in a specific response to an antigen, comprising:
    a. exposing a mammalian host to said antigen;
    b. obtaining a sample of plasma or serum from host;
    c. detecting the presence of MIG in said plasma or serum and correlating the presence of MIG in said plasma or serum to said host's production of said cytokine in an antigen-specific response.
22. The immunoassay of claim 21, wherein said cytokine is IFN-γ.
23. The immunoassay of claim 21, wherein said host is selected from the group consisting of a human, non-human primate, bovine, porcine, and murine.
24. The method of claim 21, wherein said detection is accomplished by the method selected from the group consisting of by a flow based system, flow cytometry, RT/PCR, and ELISA.
25. An immunoassay method for detecting IFN-γ or IFN-γ-secreting cells, comprising:
    a. obtaining a tissue sample from a host which has been exposed to an antigen;
    b. culturing said sample in the presence of said antigen;
    c. detecting expression in said sample of a chemokine whose production is upregulated by IFN-γ; and
    d. correlating said detection to the presence of IFN-γ or IFN-γ-secreting cells in said sample, wherein said IFN-γ is secreted by said cells in an antigen-specific response.
26. The immunoassay of claim 25, wherein said host is selected from the group consisting of, human, non-human primate, bovine, porcine, and murine.

27. An immunoassay for detecting IFN-γ, or cells which secrete IFN-γ, comprising:
    obtaining a sample including peripheral blood mononuclear cells from a human host which has been exposed to an immunoreactive peptide;
    culturing said sample for a period of 4 to 16 hours in the presence of said peptide;
    detecting MIG expression in said sample via flow cytometry; and
    correlating said detection to the presence in said sample of IFN-γ or cells that secrete IFN-γ;
    wherein said expression of MIG is genetically and specifically restricted, was induced by said IFN-γ, and said induction was mediated by $CD8^+$ cells.

28. An immunoassay for detecting IFN-γ, or cells which secrete IFN-γ, comprising: Obtaining a sample including peripheral blood mononuclear cells from a human host which has been exposed to an immunoreactive peptide; culturing said sample for a period of 4-16 hours in the presence of said peptide; detecting, via flow cytometry; and correlating said detection to the presence in said sample of IFN-γ or cells that secrete IFN-γ; wherein said expression of MIG is genetically and specifically restricted, was induced by said IFN-γ, and said induction was mediated by $CD8^+$ cells.

29. A method of monitoring the immunoresponsiveness of a human subject, comprising:
    obtaining a sample of serum or plasma from a human subject that has been exposed to a known antigenic substance;
    detecting MIG in said sample; and
    correlating said detection to the immunoresponsiveness of said human subject to said antigenic substance.

30. An immunoassay for detecting IFN-γ, or cells which secrete IFN-γ, comprising:
    obtaining a sample including peripheral blood mononuclear cells from a human host which has been exposed to an immunoreactive peptide;
    culturing said sample for a period of 4 to 16 hours in the presence of said peptide;
    detecting MIG expression in said sample via flow cytometry; and
    correlating said detection to the presence in said sample of IFN-γ or cells that secrete IFN-γ;
    wherein said expression of MIG is genetically and specifically restricted, was induced by said IFN-γ, and said induction was mediated by $CD4^+$ cells.

31. An immunoassay method for detecting a chemokine, a Th-1 cytokine that induces expression of said chemokine, or cells which secrete said Th-1 cytokine that induces expression of said chemokine, comprising:
    obtaining a tissue sample from a mammalian host which has been exposed to an antigen;
    culturing said tissue sample in the presence of said antigen;
    detecting expression of said chemokine in said sample; and
    correlating said detection to the presence of said Th-1 cytokine which induces expression of said chemokines, or cells that secrete said cytokine that induces expression of said chemokine,
    wherein said Th-1 cytokine is secreted by said cells in an response to said antigen.

32. The method of claim 1, wherein said MIG expression is antigen-specific or genetically-restricted.

33. The method of claim 13, wherein said MIG expression is antigen-specific or genetically-restricted.

34. The method of claim 1, wherein said tissue sample is cultured for 4-20 hours.

35. The method of claim 25, wherein said detection is accomplished by the method selected from the group consisting of a flow based system, flow cytometry, RT/PCR, and ELISA.

* * * * *